United States Patent [19]

Garritano

[11] Patent Number: 4,501,155

[45] Date of Patent: Feb. 26, 1985

[54] COMPENSATED RHEOMETER

[75] Inventor: Ronald F. Garritano, Flemington, N.J.

[73] Assignee: Rheometrics, Inc., Piscataway, N.J.

[21] Appl. No.: 509,219

[22] Filed: Jun. 29, 1983

[51] Int. Cl.³ .............................................. G01N 3/22
[52] U.S. Cl. ................................................. 73/847
[58] Field of Search ........................ 73/60, 847, 1 R; 374/48

[56] References Cited

U.S. PATENT DOCUMENTS 1,327,838  1/1920  Naylor ................................. 73/847

3,696,664  10/1972  Moser et al. .......................... 73/847

*Primary Examiner*—Anthony V. Ciarlante
*Attorney, Agent, or Firm*—Samuelson & Jacob

[57] ABSTRACT

A rotational rheometer utilizes a rotor coupled to a test specimen and suspended in a stator by a low friction bearing suspension system, a compensation arrangement which compensates for bearing torque on the rotor throughout the full range of rotation of the rotor, and position transducers arranged for determining accurately both the angular position of the rotor throughout a full range of 360° of rotation, and the longitudinal position of the rotor, relative to the stator.

21 Claims, 4 Drawing Figures

COMPENSATED RHEOMETER

The present invention relates generally to the evaluation of rheological characteristics of test specimens and pertains, more specifically, to a rotational rheometer in which a precise torque is applied to a rotor coupled to a test specimen while strain is monitored in the test specimen.

Rotational rheometers have been available for many years for use in the analysis of rheological properties of a wide variety of materials. In evaluating these rheological properties, it is important to maintain the stresses and strains in the test specimens at a relatively low level so as to remain within the Newtonian or zero shear rate range for polymer melts or polymer solutions, and in the linear viscoelastic region for structured materials, such as colloidal suspensions. Such low levels of stress and strain place stringent requirements on the rheometer in order to attain accuracy, since the effects of friction among the moving components of the rheometer are most noticeable at these low levels and can introduce significant errors in measurements. Since frictional forces usually are associated with the application of stress to a test specimen, most rheometers have been operated so as to place a predetermined strain or strain rate in a test specimen and to then measure the resulting stress.

However, it has been found advantageous, from the standpoint of shortening the time required for performing particular rheological tests, to apply a precise stress to a test specimen and then measure the resulting strain. It has been demonstrated that under these circumstances, the various forces in the test specimen will come to equilibrium more quickly, providing accurate test results in a more expeditious manner. Furthermore, accuracy is increased by virtue of the fact that strain can be measured more easily as a function of time with precision than stress. Moreover, when operating in the recovery mode, that is, where a test specimen is allowed to recover with no stress applied, while strain is monitored, the ability to measure strain in the absence of stress enables an evaluation of the elastic component of the modulus or compliance of the material, independent of the viscous component, since the recovery strain is purely a function of that elastic component. Thus, even materials having a very low elastic component, as compared to the viscous component, can be evaluated accurately with an instrument which will allow the accurate monitoring of strain during recovery with no stress applied.

Therefore, it would be advantageous to have available a rotational rheometer which would effectively apply a precise stress to a test specimen and enable accurate measurement of the resulting strain without the adverse effects of frictional forces among the moving components of the instrument. A rotational rheometer having such capabilities would require an essentially frictionless system for suspending and driving the rotor of the instrument relative to the stator of the instrument. Furthermore, the instrument should be capable of applying a precise stress and of monitoring strain accurately throughout a full range of 360° of rotation of the rotor, thereby providing increased versatility for testing a wider variety of materials. Additionally, the ability to accurately monitor strain during recovery of the material of the test specimen, would be a valuable asset.

It has been suggested that an appropriate frictionless suspension system could be provided through the use of a very low friction bearing, such as an aerostatic or gas-lubricated bearing, commonly known as an air bearing. However, the use of such low friction arrangements tends to introduce unwanted bearing torques resulting from the characteristics of the bearing arrangements themselves, which bearing torques, while of low magnitude, nevertheless become a significant factor in the range of measurements dealt with in the instrument of the present invention. For example, in an air bearing, air under pressure is passed through a small clearance between juxtaposed bearing surfaces. In order to provide the high bearing stiffness required for the rheological testing of certain materials, such as plastic melts, the clearance must be very small. Consequently, the velocity of the air passing through the small clearance is very high. Any deviation in the bearing surfaces from ideal surface contours can result in forces generated by the interaction between the high velocity airflow and the surface deviations. Since the deviations in the bearing surfaces are a function of such factors as machining accuracy, surface finish and wear, as a practical matter these deviations cannot fully be removed and the resulting forces cannot totally be eliminated. These forces will create unwanted torque applied to the rotor and the torque will vary in magnitude over different orientations of the rotor relative to the stator, thereby affecting the accuracy of the instrument. In other low friction bearing arrangements, such as in a magnetic bearing arrangement, unwanted bearing torque can be created by variations in reluctance at different orientations of the rotor relative to the stator, again affecting the accuracy of the instrument.

It would be advantageous to have available a rotational rheometer incorporating the advantages of the essentially frictionless suspension system provided by a very low friction bearing, such as an air bearing arrangement, without the disadvantages of such an arrangement, especially where the rheometer is to be used to apply a precise stress to a test specimen while measuring strain throughout a full range of 360° of rotation, and to monitor strain during recovery, with essentially no stress applied to the test specimen.

It is an object of the present invention to provide a rotational rheometer in which a precise stress may be applied to a test specimen while strain is measured throughout a full 360° of rotation.

Another object of the invention is to provide a rotational rheometer in which strain can be monitored during recovery of a test specimen, with no stress applied to the test specimen, throughout a full range of 360° of rotation.

Another object of the invention is to provide a rotational rheometer which utilizes a very low friction bearing, such as an air bearing arrangement, to attain an essentially frictionless suspension system for the rotor of the instrument, compensated for deviations ordinarily found in such bearing arrangements.

Still another object of the invention is to provide a rotational rheometer of the type described and in which a particular arrangement of rotational transducers provides an accurate, compensated indication of the angular position of the rotor of the instrument at any particular angular position within a full 360° range.

Yet another object of the invention is to provide a rotational rheometer of the type described and in which a linear transducer provides an accurate indication of the longitudinal position of the rotor of the instrument.

A further object of the invention is to provide a rotational rheometer which is easier to use and enables increased accuracy in results with less complex operating procedures.

A still further object of the invention is to provide a rotational rheometer which permits increased accuracy over a wider range of operation.

Yet a further object of the invention is to provide a rotational rheometer of the type described and which is relatively simple in construction and relatively inexpensive to manufacture.

The above objects, as well as still further objects and advantages, are attained by the present invention which may be described briefly as an improvement in an apparatus for the evaluation of rheological characteristics of a test specimen through analysis of torsional forces and angular positions in a rotor coupled to the test specimen and suspended within a stator by a low friction bearing for rotation relative to the stator within a range of angular positions about a longitudinal axis of rotation and in a predetermined longitudinal position along the longitudinal axis, the nature of the bearing being such that bearing torque is applied to the rotor at at least some of the angular positions, the apparatus including force-applying means for applying selected torque to the rotor at any of the angular positions, the improvement comprising: command means for defining selected angular positions of the rotor within the range of angular positions thereof; position-determining means for determining the actual angular position of the rotor relative to stator throughout the range of angular positions; bearing compensation means coupled to the force-applying means, the command means and the position-determining means for actuating the force-applying means in response to compensation information derived from deviations from any one selected angular position of the rotor and a corresponding actual angular position to balance the rotor at the one selected angular position against the bearing torque at the one selected angular position; and storage means for storing such compensation information for a plurality of selected angular positions of the rotor, whereby compensation information is made available for balancing the rotor against the bearing torque at any selected angular position within the range of angular positions.

The invention will be understood more fully, while still further objects and advantages thereof will become apparent, in the following detailed description of a preferred embodiment illustrated in the accompanying drawing, in which.

Figure 1:
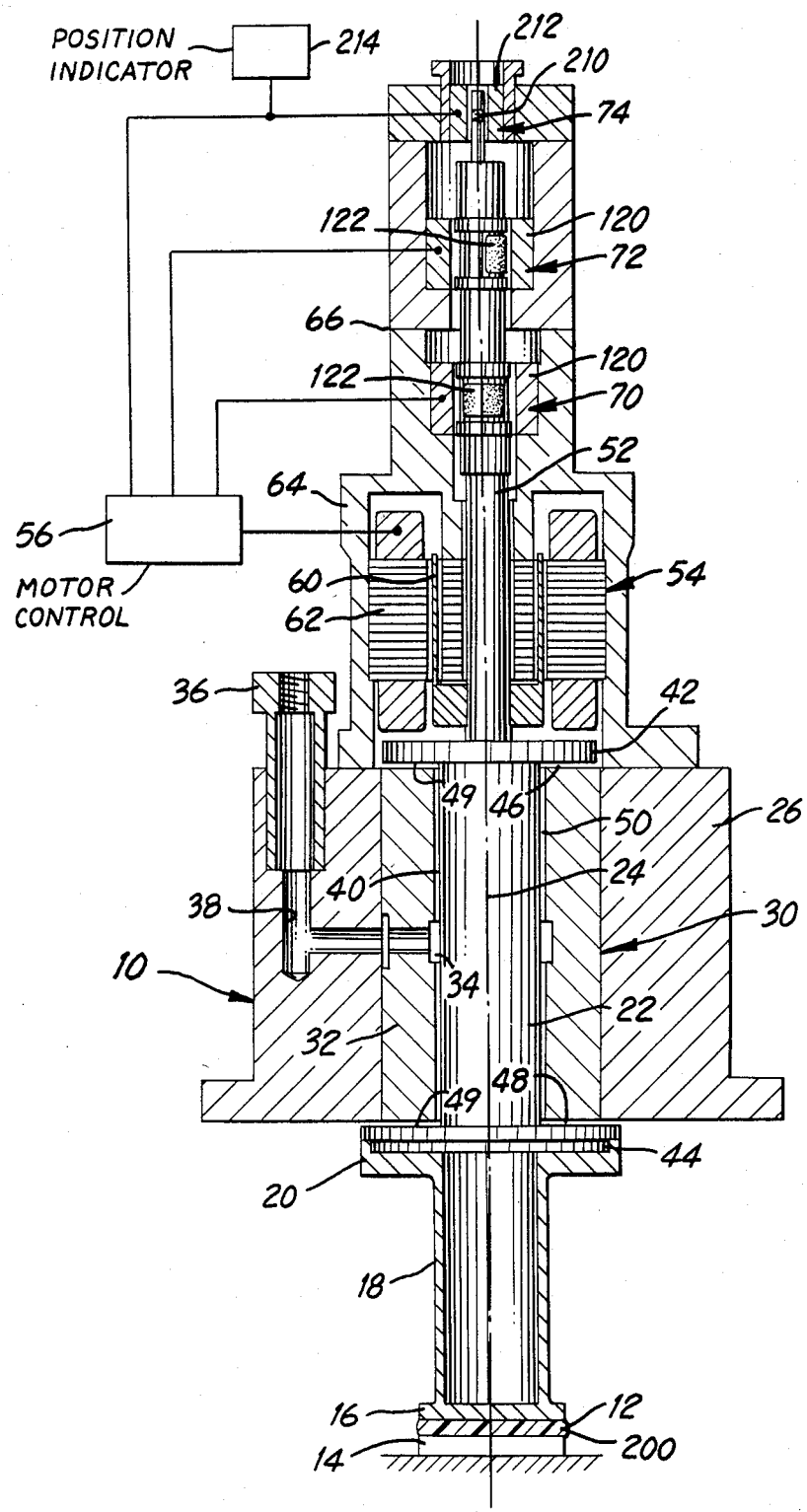
FIG. 1 is a partially diagrammatic longitudinal cross-sectional view of an apparatus constructed in accordance with the invention.

Referring now to the drawing, and especially to FIG. 1 thereof, an apparatus constructed in accordance with the invention is illustrated in the form of rotational rheometer 10 and is seen to be coupled to a test specimen 12 for the evaluation of rheological characteristics of the test specimen 12. While test specimens may take any one of several different configurations, test specimen 12 is shown in the form of a disk of polymer secured to a fixed table 14 and coupled to a platen 16 of rheometer 10 carried by a tubular carrier 18 having a flange 20 secured to a central rotor 22 of rheometer 10. Where the test specimen has a different configuration, table 14 and platen 16 will be made to conform to that configuration.

Rotor 22 extends longitudinally in a vertical direction along a central longitudinal axis 24 and is suspended for rotation about longitudinal axis 24 within a stator 26 by means of a very low friction bearing, in this instance the bearing being an aerostatic or gas-lubricated bearing shown in the form of a linear air bearing 30. Air bearing 30 includes a sleeve 32 having a centrally-located annular passage 34 communicating with an air inlet fitting 36 through a supply passage 38. Air under pressure, typically about 80 psi, is supplied at inlet fitting 36 and flows through supply passage 38 and annular passage 34 into a small axially-extending annular clearance 40 between the rotor 22 and sleeve 32, at either side of annular passage 34, toward opposite upper and lower thrust plates 42 and 44, respectively, where the air flows radially outwardly through corresponding upper and lower radially-extending clearances 46 and 48 to exit to the ambient atmosphere. Thrust plates 42 and 44 are integral with rotor 22 and provide radial bearing surfaces 49 at opposite ends of an axial bearing surface 50 along rotor 22 so that the air passing through clearances 40, 46 and 48 establishes a thin film which supports the rotor 22 in essentially frictionless suspension within stator 26.

A central shaft 52 is integral with rotor 22 and extends longitudinally upwardly along axis 24 to provide for the rotation of rotor 22 within stator 26. A motor 54 is controlled by a control 56 to apply torque to shaft 52, and hence to rotor 22. Motor 54 is of the drag cup type having a drag cup rotor 60 affixed to shaft 52 and extending axially into a drag cup stator 62 secured to stationary housing 64. Central shaft 52 extends upwardly beyond drag cup motor 54 to a transducer section 66 in which there is located shaft position transducers 70, 72 and 74 for providing information pertaining to the angular position of shaft 52 about axis 24 and the longitudinal position of shaft 52 along axis 24, as will be explained in greater detail below.

In the use of rheometer 10, the torque applied to the rotor 22 by drag cup motor 54 at specific angular positions of the rotor 22 relative to stator 26 becomes the actual basis upon which the analysis of rheological characteristics of the specimen 12 rests. Thus, a precise torque applied to shaft 52 by motor 54 can be used to apply a predetermined stress to the test specimen, and rotational displacement of the shaft 52 is measured to determine strain. In another mode of operation, the test specimen 12 is allowed to recover, with no stress applied to the test specimen, and strain is monitored. In both modes of operation, rotational displacement of rotor 22 can take place through a full 360° range of displacement. While the use of a low friction bearing such as air bearing 30 reduces frictional forces so as to eliminate inaccuracies due to bearing torque, there are certain characteristics of such low friction bearings, as discussed above, which could introduce errors. Compensation for these errors is provided by the present arrangement.

For example, in connection with air bearing 30, in order to provide the high bearing stiffness required for testing plastic melts in rheometer 10, the clearances 40, 46 and 48 must be limited so that the air film thickness is maintained at about eight to ten microns. As a result, even though the volume of air required is small (typically, less than about one-half standard cubic feet per minute) the velocity of the air as it flows through the clearances is quite high, usually in excess of one-hundred miles per hour. Such high velocity flow creates considerable drag or frictional forces on the bearing surfaces, and particularly along bearing surfaces 49 and 50. Air bearing 30 is designed and precision machined in an effort to confine the flow of air to axial flow along surface 50 and radial flow along surfaces 49, with no flow in circumferential directions which would result in unwanted torque on rotor 22 and concomitant stress in the test specimen 12 arising out of the frictional forces induced by the high velocity air flow. However, the realities of machining accuracy and surface finish on the relevant bearing surfaces, as well as minute machining imperfections and wear marks can and do result in the introduction of bearing torque which can have a significant effect upon the accuracy of the rheometer. Since the effect of these various imperfections will vary from position to position around the full 360° movement of the rotor 22 relative to stator 26, the magnitude of the unwanted bearing torque will vary from position to position. In order to optimize the accuracy of rheometer 10, compensation means is provided to compensate for the above characteristics of air bearing 30.

Figure 2:
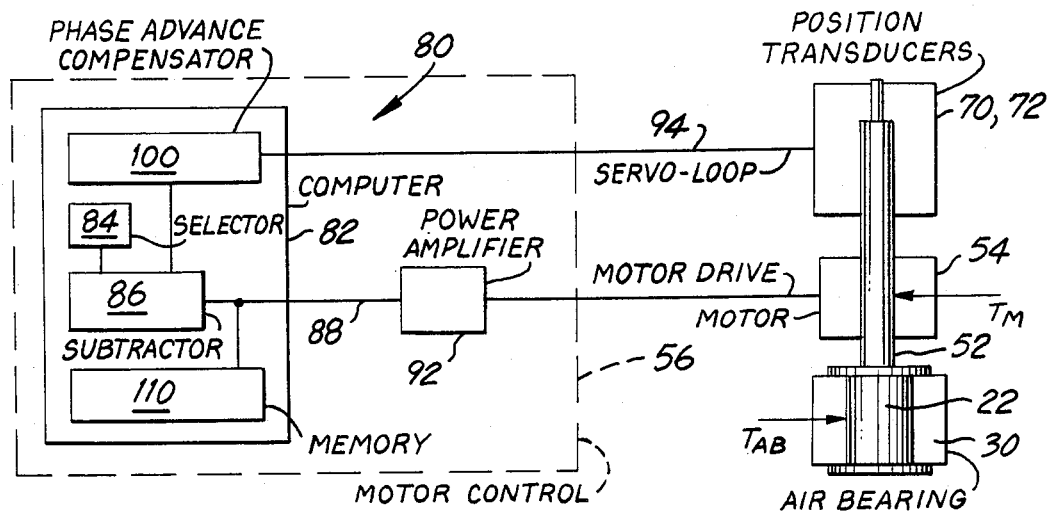
FIG. 2 is a block diagram illustrating the compensation system of the apparatus.

Turning now to FIG. 2, as well as to FIG. 1, control 56 includes a compensation system, shown diagrammatically at 80, which is operated prior to any test being performed on a test specimen in order, in essence, to calibrate the air bearing 30 so that proper compensation will be available for use during a test. In the compensation system 80, the motor 54 is used in a servo-loop to drive the rotor 22 to selected angular positions. At each of those positions, the compensation system assures that the torque applied to the rotor 22 by the motor 54 will oppose exactly the unwanted torque exerted on the rotor 22 by the forces generated in the air bearing 30 at that position.

In the calibration mode, a computer 82 employs a program-operated selector element 84 to generate a command to move the rotor 22 to a selected angular position. The actual angular position of the rotor, as determined by the shaft position transducers 70 and 72, is compared with the commanded position at a program-operated subtractor element 86 and any difference determined by subtractor element 86 provides a signal at 88 which is used to generate a torque in the motor 54 to drive the difference to zero. The signal at 88 passes to a power amplifier 92 which drives the motor 54. A servo-loop 94 includes a program-operated phase advance compensation element 100 provided for stabilizing the servo-loop 94. When rotor 22 reaches the selected command position, the resultant torque on the rotor 22 is zero and the motor output torque $T_M$ exactly opposes the unwanted air bearing torque $T_{AB}$. Thus, the signal provided at 88 results in a torque applied to rotor 22 and, for each selected position of the rotor 22, the signal at 88 will provide a requisite torque to oppose exactly the unwanted air bearing torque at that position. As the commanded position is stepped through the plurality of selected positions by selector element 84, the corresponding signals 88 are stored in a memory 110 to obtain a complete catalogue of compensation torques which correspond to the unwanted torques applied by the air bearing 30 at the various rotor positions. The catalogue is used subsequently to correct or compensate torque measurements taken or torque applied during an actual test so as to eliminate any error which might otherwise result from air bearing torque.

The advantages inherent in compensation system 80 include the ability to calibrate rheometer 10 prior to any test without the need for added hardware or other components and concomitant set up time. Furthermore, the bearing torque is determined by the same component which is used to apply torque to the rotor 22 during regular operating modes, namely, motor 54. Thus, any errors inherent in the device itself, such as linearity and absolute accuracy, are cancelled. The ability to operate rheometer 10 independent of component errors is particularly advantageous in the mode of operation where zero stress is to be applied to the test specimen, as described above. Compensation system 80 thus is available for use in compensating for unwanted bearing torque in connection with essentially all low friction bearing arrangements where bearing torque will vary with rotor position.

The versatility and accuracy of rheometer 10 are largely dependent upon the manner in which the actual position of rotor 22 is determined. Thus, the rotor position transducers 70, 72 and 74 are selected on the basis of sensitivity, accuracy and reliability, as well as cost considerations. The transducers must provide a high degree of resolution and should not introduce any significant inertia effects to the rotor 22 and shaft 52 arrangement. As set forth above, transducers 70 and 72 are employed to define the particular angular position of rotor 22 about longitudinal axis 24 relative to stator 26, while transducer 74 is used for determining the longitudinal position of rotor 22 along axis 24. Looking first at the problem of determining the angular position of rotor 22, a variety of resolvers and synchros have been available for some time for measuring continuous angular positions of rotating elements. These components essentially are inductive devices having multiple outputs, representing trigonometric functions of the angular positions, which can be converted to direct angle units using computer software. Such devices usually employ wound rotors with concomitant high inertia and require slip rings or another form of commutator to obtain the necessary position information. Slip rings, commutators and other like devices inherently introduce static friction and are not appropriate in the present system. Brushless resolvers using permanent magnet rotors are available, but such devices introduce reluctance torques which cause preferred rotor orientation and interfere with accurate measurements.

The preferred transducer for use in the present system is a rotary variable differential transformer (RVDT). An RVDT provides low cost, very low inertia, continuous information for infinite resolution, and requires no mechanical-electrical contact with the rotating element of the device. An RVDT employs a small core of ferromagnetic material, which usually is mounted upon the component whose rotation is to be measured, and a wound differential transformer which is stationary and located adjacent the core. Movement of the core within the stationary transformer in effect changes the coupling coefficient between the primary and secondary windings of the transformer, resulting in a linear output proportional to displacement. A linear output is limited, however, to displacements of 120° around a zero position and 120° around a diametrically opposite (180°) position. Thus, rheometer 10 employs two RVDT devices, in the form of transducers 70 and 72, located 90° apart around axis 24 and computer software to combine the outputs of both transducers 70 and 72 into one continuous output over the full 360° rotation of rotor 22 and shaft 52, with no discontinuities. Each transducer 70 and 72 includes a stationary transformer 120 affixed to the housing 64 of the rheometer 10, and a movable core 122 attached to the shaft 52 for rotation within the transformer 120.

Figure 3:
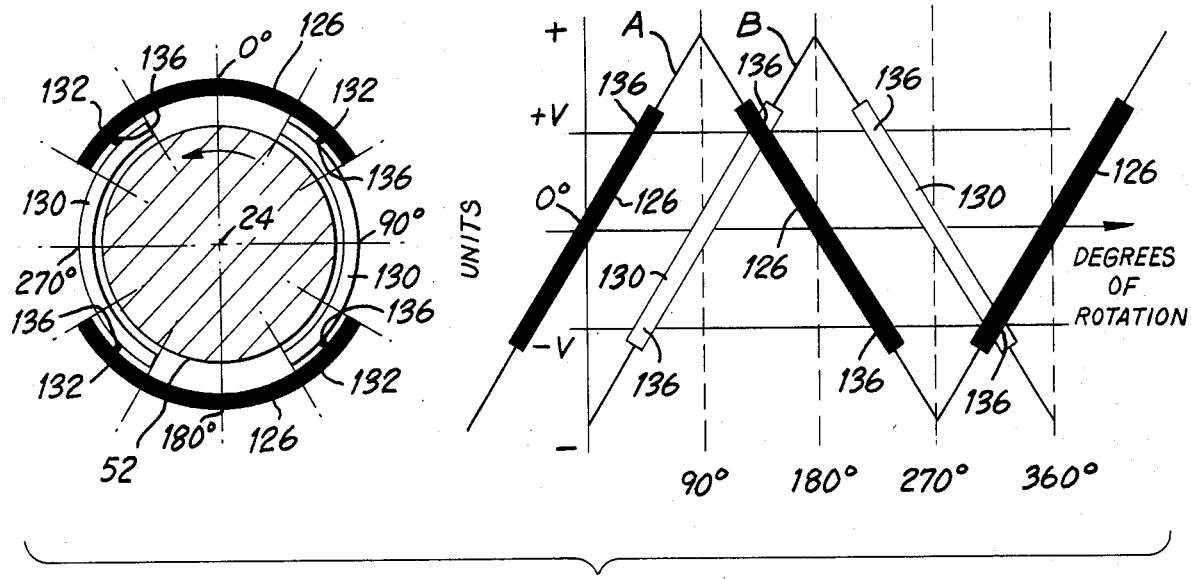
FIG. 3 is a diagrammatic illustration of the position transducer arrangement of the apparatus.

As seen diagrammatically in FIG. 3, transducer 70 provides a linear output signal A throughout ranges of rotation of shaft 52, and rotor 22, limited to 120° segments 126 oriented symmetrically about the 0° and 180° positions of shaft 52. Transducer 72 likewise provides an output signal B throughout ranges of rotation of shaft 52, and rotor 22, limited to 120° segments 130. However, transducer 72 is located relative to tranducer 70 at an angle of 90° thereto so that the segments 130 are oriented symmetrically about the 90° and 270° positions of shaft 52. In this manner, the output signals A and B overlap to provide a linear, error-free output throughout 360° of rotation of shaft 52.

However, a problem arises when there is a transition from one output signal A or B to the other ouput signal. Thus, in order to obtain a continuous output signal throughout 360° of rotation of shaft 52, and rotor 22, the output signal is switched from one output signal A or B to the other output signal within the regions 132 where the output signals overlap. Regions 132 each should lie within a 30° segment where the segments 126 and 130 would be aligned perfectly relative to one another; however, perfect alignment is not always attained, due to manufacturing tolerances. Therefore, the output signals A and B at any single angular position within the regions 132 will not necessarily be of identical magnitude. Hence, when switching from one output signal to the other, there may be an immediately perceptible difference in the magnitude of the output signal being monitored, resulting in an unwanted discontinuity. Moreover, even if perfect alignment of the segments 126 and 130 could be attained, differences would appear in the output signals A and B at any single angular position within the regions 132 as a result of thermal drift, aging and electrical noise or other distortion.

Figure 4:
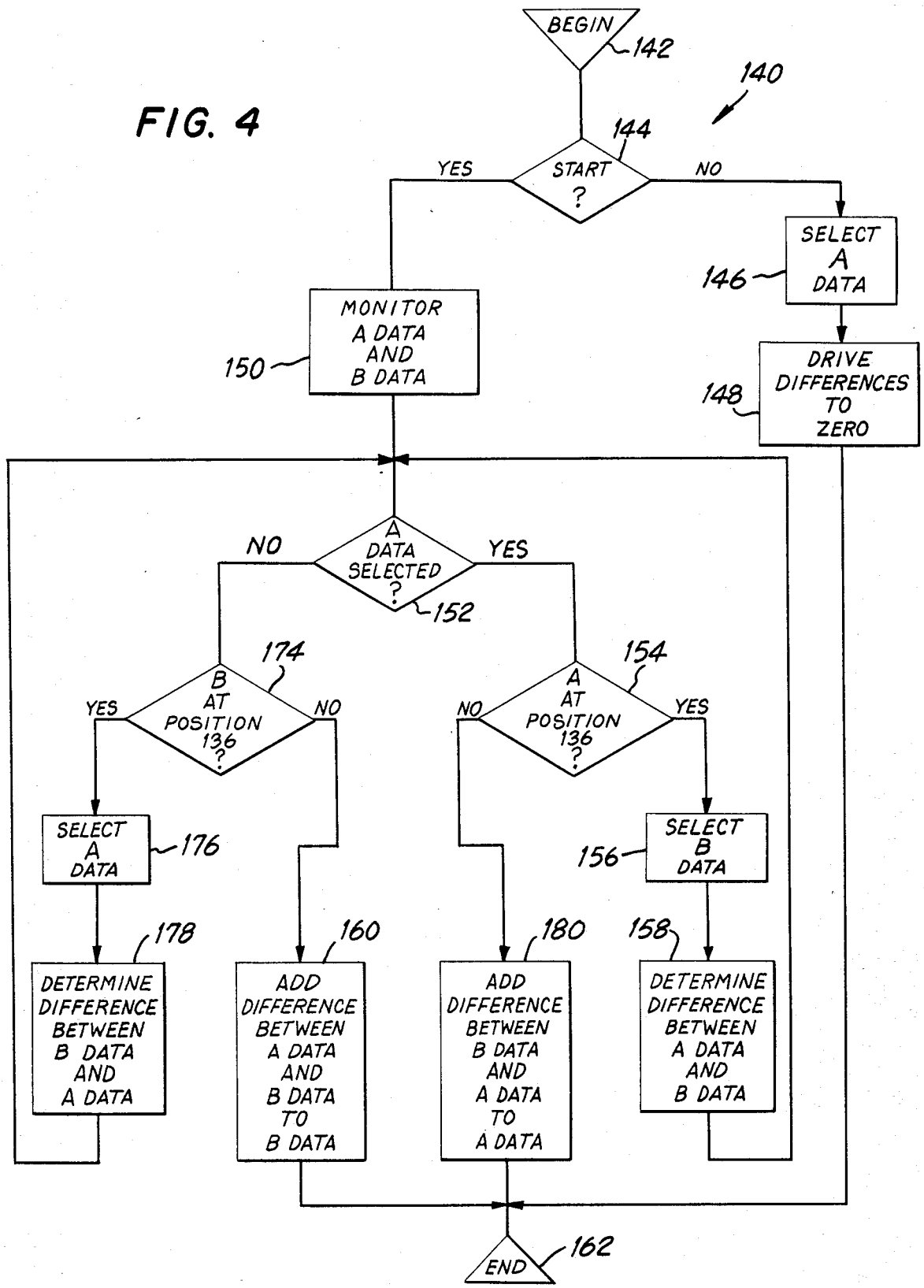
FIG. 4 is a flow chart showing the operation of the position transducer compensation system of the apparatus.

In order to overcome the above problem, the output signals A and B are switched in response to a software program, illustrated in FIG. 4. Switching takes place at angular positions designated as positions 136 in FIG. 3. Positions 136 are located at 45° to either side of the 0° and 180° positions, placing the positions 136 well within the regions 132. Thus, as seen in FIG. 3, a position 136 is located at 45°, 135°, 225° and 315°. At positions 136, the absolute magnitudes of output signals A and B should be equal, but may be of opposite polarity. In the diagram of FIG. 3, output signal A at 45° is +V, while output signal B is −V. At 135° signals A and B both are +V. At 225° signal A is −V while signal B is +V. At 315°, both output signals A and B are −V. Since there probably will be deviations from the ideal matching of the magnitudes of output signals A and B at the switching positions 136, for the reasons outlined above, software program 140, shown in FIG. 4, compensates for such deviations.

Thus, a computer is employed to track signals A and B at all times and is operated in accordance with software program 140 to compute any difference between the absolute magnitudes of output signals A and B at each angular position 136 just prior to switching from one output signal A or B to the other, and to add that difference to the other output signal immediately after switching so as to assure continuity through the transition from one output signal to the other. The computed difference remains added to the other output signal until the next transition at the next position 136 where a new difference is computed for the next switch. The arrangement has been found to operate successfully within alignment errors of as much as three degrees.

Software program 140 illustrates the above compensation routine. Program 140 begins at 142. An operator selectively initiates the program routine at start 144. Prior to initiating the routine at start 144, the program is self-initiated to select data provided by signal A, at 146, and any differences between the data provided by signals A and B are driven to zero, as illustrated at 148. Once the routine is started at 144, the data provided by both signals A and B is monitored at 150. The determination at 152 that signal A data has been selected enables the program to monitor the signal A data at 154 until it is determined that a switching position 136 has been reached. Upon reaching a switching position 136 where the polarities of signals A and B differ, data provided by signal B is selected, as shown at 156, and any difference between the data provided by signals A and B at that position 136 is determined at 158 and is added at 160 to the data provided by signal B. The data from which angular position information is obtained then is provided at 162. While the signal A data remains within the range of a segment 126 between switching points 136, the angular position information provided at 162 is determined by the data provided by signal A. Likewise, when it is determined at 152 that the data from signal A is not selected, the data from signal B is monitored at 174 until it is determined that a switching position 136 has been reached. Upon reaching a switching position 136 where the polarities of signals A and B are the same, data provided by signal A is selected, as shown at 176, and any difference between the data provided by signals A and B at that position 136 is determined at 178 and is added at 180 to the data provided by signal A. Again, while the signal B data remains within the range of a segment 130 between switching points 136, the angular position information provided at 162 is determined by the data provided by signal B. By adding the differences each time there is a switch from one to the other of signals A and B, a continuous, uninterrupted transition is assured. It is noted that in the switching routine described above, switching occurs during rotation of shaft 52 in the direction shown in FIG. 3. Should the signals A and B be tracked during rotation in the opposite direction, switching from signal A to signal B will take place when the polarities of signals A and B are the same, while switching from signal B to signal A will occur when the polarities differ. Routine 140 therefore takes into account the direction of rotation of shaft 52.

An important requirement in rheometer 10 is the accurate determination of the longitudinal position of platen 16 relative to table 14. Measurement of that position determines the geometry of test specimen 12 for converting the angular position of rotor 22, and shaft 52, and torque measurements to stress and strain in the test specimen. The gap 200 between the platen 16 and table 14 is selectively varied by longitudinal movement of the entire assembly which includes housing 64, shaft 52, rotor 22 and carrier 18, relative to table 14, and the position of platen 16 relative to table 14 is measured by a micrometer (not shown), usually mounted upon the same assembly. It is necessary, however, to set the micrometer to zero when the platen 16 and the table 14 just touch. The determination of this zero point, the point at which the platen 16 and the table 14 just touch, must be accomplished with great accuracy.

It has been suggested that an electrical circuit can be utilized to detect electrical contact between the platen and the table. Such a system requires electrical connections to the platen, which connections cannot be present during testing and must therefore be removed prior to running any actual test. Furthermore, electrical contact information merely indicates contact or no contact and would provide no information concerning axial displacement of the platen 16 relative to the housing 64 as a result of compression of the air film in clearance 48 as housing 64 moves downwardly beyond the zero point, so that the actual zero point readily is bypassed.

In order to attain an accurate determination of the zero point, rheometer 10 employs shaft position transducer 74 to provide an indication of axial movement of shaft 52 relative to housing 64. Preferably, transducer 74 is a linear variable differential transformer (LVDT) which utilizes a relatively lightweight core 210 affixed to shaft 52 and surrounded by a wound differential transformer 212 held stationary in housing 64. The output of the transducer 74 drives an indicator 214 which is set to zero when the platen 16 is not touching anything and the rotor 22 is in its normal longitudinal position, suspended in the stator 26 by air bearing 30. Once the platen 16 is brought into contact with table 14, the rotor 22, and shaft 52, can be moved axially relative to stator 26 and housing 64, as a result of the compressibility of the air film in clearance 48 of air bearing 30. Such axial movement will be detected by transducer 74 and transmitted to indicator 214. The indicator 214 is calibrated directly in distance deviations from the zero point and the zero point is determined with great accuracy.

It is to be understood that the above detailed description of an embodiment of the invention is provided by way of example only. Various details of design and construction may be modified without departing from the true spirit and scope of the invention as set forth in the appended claims.

The embodiments of the invention in which an exclusive property or privilege is claimed are as follows:

1. In an apparatus for the evaluation of rheological characteristics of a test specimen through analysis of torsional forces and angular positions in a rotor coupled to the test specimen and suspended within a stator by a low friction bearing for rotation relative to the stator within a range of angular positions about a longitudinal axis of rotation and in a predetermined longitudinal position along the longitudinal axis, the nature of the bearing being such that bearing torque is applied to the rotor at at least some of the angular positions, the apparatus including force-applying means for applying selected torque to the rotor at any of the angular positions, the improvement comprising:

command means for defining selected angular positions of the rotor within the range of angular positions thereof;

position-determining means for determining the actual angular position of the rotor relative to the stator throughout the range of angular positions;

bearing compensation means coupled to the force-applying means, the command means and the position-determining means for actuating the force-applying means in response to compensation information derived from deviations from any one selected angular position of the rotor and a corresponding actual angular position to balance the rotor at the one selected angular position against the bearing torque at the one selected angular position; and storage means for storing such compensation information for a plurality of selected angular positions of the rotor, whereby compensation information is made available for balancing the rotor against the bearing torque at any selected angular position within the range of angular positions.

2. The invention of claim 1 wherein the bearing compensation means includes servo-loop means for deriving the compensation information.

3. The invention of claim 1 or 2 wherein the range of angular positions of the rotor extends throughout 360° of rotation.

4. The invention of claim 3 wherein the position-determining means includes at least one rotary variable differential transformer placed between the rotor and the stator.

5. The invention of claim 1 wherein the position-determining means includes at least one angular position transducer responsive to the relative positions of the rotor and the stator for providing position data pertaining to the angular position of the rotor relative to the stator.

6. The invention of claim 5 wherein the one angular position transducer provides position data pertaining to the angular position of the rotor relative to the stator within a first range of angular positions extending through less than 360° of angular movement of the rotor relative to the stator and the apparatus includes a second angular position transducer for providing further position data pertaining to the angular position of the rotor relative to the stator within a second range of angular positions supplemental to the first range such that the first and second ranges together extend throughout 360° of angular movement of the rotor relative to the stator.

7. The invention of claim 6 including
   information means for providing position information pertaining to the angular position of the rotor, based upon position data received from either one of the angular position transducers;

monitoring means for monitoring the position data provided by both angular position transducers within both of the ranges;

switching means for switching the position data received by the information means from one of the angular position transducers to the other in response to the location of the rotor at a predetermined angular position;

difference means for determining any difference between the position data provided by each of the angular position transducers at the predetermined angular position; and data compensation means for combining the difference between the position data at the predetermined angular position with the position data provided by the other angular position transducer to effect a compensated transition between position data received by the information means from one and then the other of the angular position transducers throughout the first and second ranges.

8. The invention of claim 5, 6 or 7 wherein each angular position transducer comprises a rotary variable differential transformer placed between the rotor and the stator.

9. The invention of claim 8 wherein the first and second ranges of angular positions overlap at regions and each predetermined angular position is located within one of the regions.

10. The invention of claim 9 wherein the first and second ranges each extend over diametrically opposed segments.

11. The invention of claim 10 wherein the diametrically opposed segments each extend over about 120° and the rotary variable differential transformers are spaced about 90° apart around the longitudinal axis.

12. The invention of claim 1 including a linear position transducer responsive to the relative longitudinal positions of the rotor and the stator for providing position data pertaining to the longitudinal position of the rotor relative to the stator, and indicator means coupled to the linear position transducer for indicating the location of the rotor at the predetermined longitudinal position.

13. The invention of claim 12 wherein the bearing includes lateral bearing surfaces for locating the rotor in the predetermined longitudinal position and the indicator means indicates longitudinal deviations in the rotor position from the predetermined longitudinal position.

14. The invention of claim 12 or 13 wherein the linear position transducer comprises a linear variable differential transformer placed between the rotor and the stator.

15. In an apparatus for the evaluation of rheological characteristics of a test specimen through analysis of torsional forces and angular positions in a rotor coupled to the test specimen and suspended within a stator by suspension means for rotation relative to the stator within a range of angular positions about a longitudinal axis of rotation and in a predetermined longitudinal position along the longitudinal axis, the apparatus including force-applying means for applying selected torque to the rotor at any of the angular positions, the improvement comprising:
   a first angular position transducer for providing position data pertaining to the angular position of the rotor relative to the stator within a first range of angular positions extending through less than 360° of angular movement of the rotor relative to the stator;
   a second angular position transducer for providing further position data pertaining to the angular position of the rotor relative to the stator within a second range of angular positions supplemental to the first range such that the first and second ranges together extend throughout 360° of angular movement of the rotor relative to the stator;
   information means for providing position information pertaining to the angular position of the rotor, based upon position data received from either one of the angular position transducers;

monitoring means for moniforing the position data provided by both angular position transducers within both of the ranges;
   switching means for switching the position data received by the information means from one of the angular position transducers to the other in response to the location of the rotor at a predetermined angular position;
   difference means for determining any difference between the position data provided by each of the angular position transducers at the predetermined angular position; and
   data compensation means for combining the difference between the position data at the predetermined angular position with the position data provided by the other angular position transducer to effect a compensated transition between position data received by the information means from one and then the other of the angular position transducers throughout the first and second ranges.

16. The invention of claim 15 wherein each angular position transducer comprises a rotary variable differential transformer placed between the rotor and the stator.

17. The invention of claim 16 wherein the first and second ranges of angular positions overlap at regions and each predetermined angular position is located within one of the regions.

18. The invention of claim 17 wherein the first and second ranges each extend over diametrically opposed segments.

19. The invention of claim 18 wherein the diametrically opposed segments each extend over about 120° and the rotary variable differential transformers are spaced about 90° apart around the longitudinal axis.

20. In an apparatus for the evaluation of rheological characteristics of a test specimen through analysis of torsional forces and angular positions in a rotor coupled to the test specimen and suspended within a stator by an air bearing for rotation relative to the stator within a range of angular positions about a longitudinal axis of rotation in a predetermined longitudinal position along the longitudinal axis, the air bearing having lateral bearing surfaces for locating the rotor in the predetermined longitudinal position by means of an air film at the lateral bearing surfaces, the improvement comprising:
   a linear position transducer responsive to the relative longitudinal positions of the rotor and the stator for providing position data pertaining to the longitudinal position of the rotor relative to the stator; and
   indicator means coupled to the linear position transducer for indicating the location of the rotor at the predetermined longitudinal position and longitudinal deviations in the rotor position from the predetermined longitudinal position.

21. The invention of claim 20 wherein the linear position transducer comprises a linear variable differential transformer placed between the rotor and the stator.

* * * * *